United States Patent
Chen (10) Patent No.: US 10,238,397 B2
(45) Date of Patent: Mar. 26, 2019

(54) VASO-OCCLUSIVE DEVICES WITH IN-SITU STIFFENING

(71) Applicants: Stryker Corporation, Kalamazoo, MI (US); Stryker European Holdings I, LLC, Kalamazoo, MI (US)

(72) Inventor: Hancun Chen, San Ramon, CA (US)

(73) Assignees: Stryker Corporation, Kalamazoo, MI (US); Stryker European Holdings I, LLC, Kalamazoo, MI (US)

(*) Notice: Subject to any disclaimer, the term of this patent is extended or adjusted under 35 U.S.C. 154(b) by 373 days.

(21) Appl. No.: 14/835,131

(22) Filed: Aug. 25, 2015

(65) Prior Publication Data

US 2016/0066918 A1   Mar. 10, 2016

Related U.S. Application Data (60) Provisional application No. 62/047,268, filed on Sep. 8, 2014.

(51) Int. Cl.
| | | |
|---|---|---|
| A61B 17/12 | (2006.01) | |
| A61L 31/02 | (2006.01) | |
| A61B 17/00 | (2006.01) | |

(52) U.S. Cl.
CPC ...... *A61B 17/1215* (2013.01); *A61B 17/1214* (2013.01); *A61B 17/12031* (2013.01);
(Continued)

(58) Field of Classification Search
CPC .......... A61B 17/1214; A61B 17/1215; A61B 17/12145; A61B 17/12168; A61B 17/12172; A61B 17/12177; A61B 2017/00831; A61B 2018/2216; A61L 31/146

See application file for complete search history.

(56) References Cited

U.S. PATENT DOCUMENTS

| | | | |
|---|---|---|---|
| 4,994,069 A | 2/1991 | Ritchart et al. | |
| 5,372,660 A * | 12/1994 | Davidson | A61L 27/06 |
| | | | 148/421 |

(Continued)

FOREIGN PATENT DOCUMENTS

EP    0824900 A2   2/1998

OTHER PUBLICATIONS

Perkins et al. Metalized Coatings for Corrosion Control of Naval Ship Structures and Components. National Materials Advisory Board. Department of Defense/NASA. Feb. 1983.*

(Continued)

*Primary Examiner* — Todd Scherbel
*Assistant Examiner* — Brooke Labranche
(74) *Attorney, Agent, or Firm* — Vista IP Law Group LLP (57) ABSTRACT

A vaso-occlusive device is constructed out of dissimilar metallic materials that are in contact or otherwise in close proximity with one another, thereby causing the device to undergo galvanic corrosion when exposed to an electrolytic medium, such as blood or other body fluid, wherein one of the dissimilar metallic materials is zirconium or zirconium alloy to create a corrosive product including zirconia having a relatively high hardness, a relatively high fracture toughness, and a relatively high stability when the device is implanted in a vasculature site, such as an aneurysm.

7 Claims, 6 Drawing Sheets

(52) U.S. Cl.
CPC .. *A61B 17/12109* (2013.01); *A61B 17/12113* (2013.01); *A61B 17/12168* (2013.01); *A61B 17/12177* (2013.01); *A61L 31/022* (2013.01); *A61B 2017/00831* (2013.01); *A61B 2017/00867* (2013.01); *A61B 2017/00964* (2013.01); *A61L 2430/36* (2013.01)

(56) References Cited

U.S. PATENT DOCUMENTS

| | | | |
|---|---|---|---|
| 6,015,424 | A | 1/2000 | Rosenbluth et al. |
| 6,156,061 | A * | 12/2000 | Wallace ........... A61B 17/12022 606/200 |
| 8,556,927 | B2 | 10/2013 | Dehnad |
| 2002/0004060 | A1 * | 1/2002 | Heublein ......... A61B 17/12109 424/422 |
| 2006/0009798 | A1 * | 1/2006 | Callister .......... A61B 17/12022 606/200 |
| 2007/0270942 | A1 | 11/2007 | Thomas |
| 2008/0160259 | A1 * | 7/2008 | Nielson ..................... A61F 2/91 428/148 |
| 2011/0238150 | A1 * | 9/2011 | Deng .................... A61L 31/022 623/1.15 |
| 2014/0358178 | A1 * | 12/2014 | Hewitt ............. A61B 17/12113 606/200 |

OTHER PUBLICATIONS

International Search Report and Written Opinion for PCT/US2015/046726, dated Mar. 23, 2016, Applicant Stryker Corporation, filed Aug. 25, 2015 (13 pages).

International search report for PCT/US2015/046726, filed Aug. 25, 2015 (dated Nov. 30, 2015) (6 pages).

* cited by examiner

VASO-OCCLUSIVE DEVICES WITH IN-SITU STIFFENING

RELATED APPLICATION DATA

The present application claims the benefit under 35 U.S.C. § 119 to U.S. provisional patent application Ser. No. 62/047,268, filed Sep. 8, 2014. The foregoing application is hereby incorporated by reference into the present application in its entirety.

FIELD OF THE INVENTION

The disclosed inventions pertain generally to vaso-occlusive devices for establishing an embolus or vascular occlusion in a blood vessel. Specifically, the disclosed inventions pertain to systems and methods for in-situ stiffening of vaso-occlusive devices.

Background

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference, describes a vaso-occlusive device that assumes a linear, helical primary shape when stretched for placement through the lumen of a delivery catheter, and a folded, convoluted secondary shape when released from the delivery catheter and deposited in the vasculature. Other vaso-occlusive devices having woven braids or embolic agents have been used in treatment of intra-vascular aneurysms.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter will stay in a desired position for releasing one or more vaso-occlusive device(s) into the aneurysm once the guidewire is withdrawn. A delivery or "pusher" wire is then passed through the micro-catheter, until a vaso-occlusive device coupled to a distal end of the delivery wire is extended out of the distal end opening of the micro-catheter and into the aneurysm. Once in the aneurysm, the vaso-occlusive devices bend to allow more efficient and complete packing. The vaso-occlusive device is then released or "detached" from the end delivery wire, and the delivery wire is withdrawn back through the catheter. Depending on the particular needs of the patient, one or more additional occlusive devices may be pushed through the catheter and released at the same site.

One well-known way to release a vaso-occlusive device from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher wire completes an electrolytic detachment circuit with a return electrode, and the detachment zone disintegrates due to electrolysis.

When the above-mentioned vaso-occlusive devices are placed within an aneurysm, they tend to induce a formation of thrombi for occlusion of the aneurysm. However, once the above-mentioned vaso-occlusive devices are delivered into an aneurysm, they may not have sufficient strength or stiffness to retain their shape within the aneurysm.

For example: U.S. Pat. No. 6,015,424 (Rosenbluth et al.) describes an occlusive device having a series of flexible chain-like segments including a metallic material, such as platinum or tungsten. Through the application of an externally-sourced current, the metallic material fuses the interlinked segments together by electrolytic corrosion. This electrolytic corrosion may cause a temporary, relative stiffening of the device. However, the corroded device also tends to quickly degrade with time, and with the influence of hemodynamic forces and thrombolytic processes, the corroded, degraded device will tend to move or change shape, e.g., through the process of seeking a minimally energetic morphology, may move out of the position in which it was originally placed.

By way of another example, U.S. Pat. No. 8,556,927 (Dehnad) describes a vaso-occlusive coil having a first metallic material in the form of platinum or platinum alloy, and a second metallic material in the form of zinc or zinc alloy, so that a chemical reaction is initiated creating a galvanic cell when the coil is deployed in an aneurysm due to the presence of electrolytic blood. Again, this galvanic corrosion may cause a temporary, relative stiffening of the device, the corroded device will also tend to quickly degrade with time and the influence of hemodynamic forces and thrombolytic processes, and tends to move or change shape after placement. In some cases, the delivered vaso-occlusive devices may even dislodge out of the sack of an aneurysm. Such difficulties can undesirably increase the time needed for performing a medical procedure, as well as further increase the risk of a thrombus formation in an unintended location in the blood vessel, as the vaso-occlusive devices migrate out of the aneurysm.

Accordingly, it would be desirable to provide vaso-occlusive devices having a more durable stiffness and structural integrity to retain their shape and position over time at a target location (e.g., within an aneurysm), minimizing undesired migrations and collapsing.

SUMMARY

In accordance with a general aspect of the disclosed inventions, a vaso-occlusive device is constructed out of dissimilar metallic materials that are in contact or otherwise in close proximity with one another, with one of the metallic materials being zirconium or zirconium alloy, thereby causing the device to undergo galvanic corrosion when exposed to an electrolytic medium, such as blood or other body fluid, to create a corrosive product including zirconium dioxide ("zirconia") when the device is implanted in a vasculature site, such as an aneurysm.

In various embodiments, the device is constructed from a plurality of wire members that are braided together or otherwise arranged into a variety of different structures and shapes suitable for use as a vaso-occlusive embolic device. For example, the device may comprise a tubular sleeve, or a coil configuration. By way of another example, the device (e.g., a braid) may be provided as an adjuvant component that at least partially surrounds and covers a separate (e.g., conventional) vaso-occlusive device. The individual wire members may be composed of a single metallic material (i.e., one of the dissimilar metals), or may be formed from a composition of materials, including but not limited to one or both of the dissimilar metals. The individual wire members may vary in length, stiffness, cross-sectional shape, size, or other physical attributes. By way of non-limiting example, individual wire members may have circular or non-circular cross-sectional shapes, such as rectangular or triangular cross-sectional shapes. For instance, some or all of the individual wire members may be flat ribbon wires. In some embodiments, individual wire members have irregular, non-uniform cross-sections that vary along the length of the wire members.

In some embodiments, the device is constructed from a plurality of metallic wire members including a first subset of wire members made from or otherwise including platinum or platinum alloy, and a second subset of wire members made from or otherwise comprising zirconium or zirconium alloy, wherein the resulting electrochemical potential difference between platinum and zirconium forms zirconia at a plurality of contact points, thereby stiffening the vaso-occlusive device when exposed to blood and other body fluid after implantation. In such embodiments, the subset of platinum or platinum alloy wires may be braided or otherwise arranged with the subset of zirconium or zirconium alloy wires so that galvanic corrosion formation of zirconia at the respective contact points occurs over time, resulting in a "progressive" in-situ stiffening of the device.

In some embodiments, a vaso-occlusive device comprises a metallic braid formed from a plurality of wire members, each wire member having an inner core material comprising a first metallic material that is at least partially coated, plated, or otherwise covered with an outer coating comprising a dissimilar metallic material. In one such embodiment, the inner core material comprises platinum, and the outer coating comprises zirconium or zirconium alloy. In another such embodiment, the inner core material comprises zirconium or zirconium alloy, and the outer coating comprises platinum. In yet another such embodiment, a first subset of the plurality of wire members have platinum or platinum alloy cores with zirconium or zirconium alloy coatings, and a second subset of the plurality of wire members have zirconium or zirconium alloy cores with platinum or platinum alloy coatings. In all such embodiments, the formation of zirconia occurs along and over the plurality of wire members, since the entire length of each wire member comprises both platinum and zirconium. A thickness of the coating material may be selected based upon a desired amount of galvanic corrosion and corrosion products to be produced. Further, the coating material may be porous, wherein a pore size and/or pore density of the coating material is selected based upon a desired amount of galvanic corrosion and corrosion products to be produced. In another embodiment of the disclosed inventions, a vaso-occlusive coil is wound from a wire member comprising a core made from a first metal or metal alloy acting as an electrolytic anode, and a coating made from a suitable dissimilar metallic material acting as electrolytic cathode.

Other and further aspects and features of embodiments of the disclosed inventions will become apparent from the ensuing detailed description in view of the accompanying figures.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

In accordance with a general aspect of the disclosed inventions, a vaso-occlusive device is constructed out of dissimilar metallic materials that are in contact or otherwise in close proximity with one another, thereby causing the device to undergo galvanic corrosion when exposed to an electrolytic medium, such as blood or other body fluid, wherein one of the dissimilar metallic materials is zirconium or zirconium alloy in order to create a corrosive product comprising zirconium dioxide ("zirconia") having a relatively high hardness, a relatively high fracture toughness, and a relatively high stability when the device is implanted in a vasculature site, such as an aneurysm.

Figure 1A:
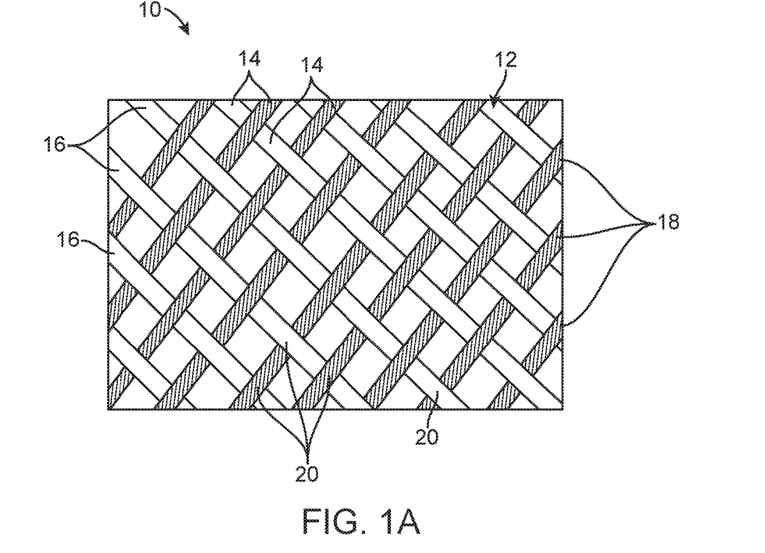
FIGS. 1A-B are perspective views of a vaso-occlusive device braid constructed according to various embodiments of the disclosed inventions.
Figure 1B:
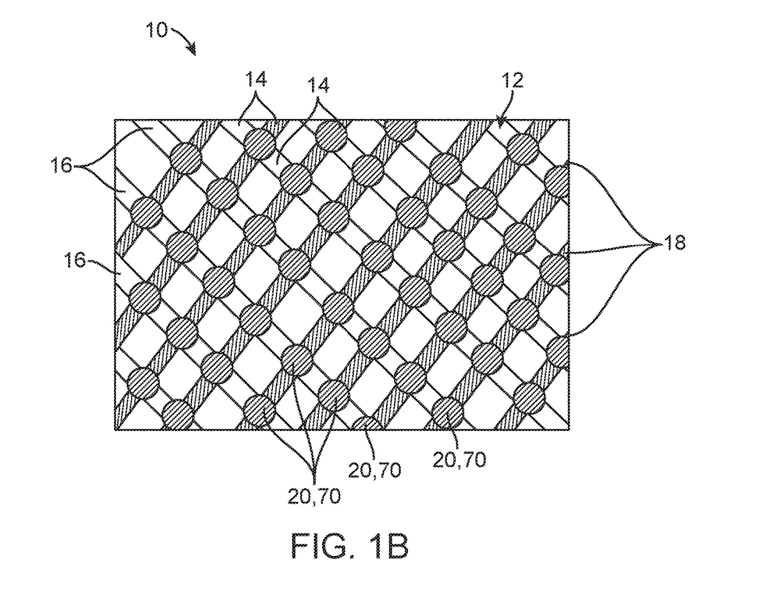

FIGS. 1A-B illustrate a vaso-occlusive device 10 constructed in accordance with various embodiments of the disclosed inventions. The vaso-occlusive device 10 comprises a metallic braid 12 formed from a plurality of elongate members (e.g., wires) 14 composed of or otherwise including zirconium or an alloy of zirconium, along with a dissimilar metallic material, such as platinum. The metallic braid 12 may have a variety of different shapes, sizes, lengths, etc., suitable for use as a vaso-occlusive device. For example, the metallic braid 12 may comprise a tubular sleeve, a coil configuration, or the braid 12 may be an adjuvant component that at least partially surrounds and covers a separate (e.g., conventional) vaso-occlusive device (FIGS. 5A-F). Individual members (hereinafter, "wire members") 14 that are woven together to form the braid 12 may be formed from a single material, such as one of the dissimilar metals, or may be formed from a composition of materials, including (but not limited to) one or both of the dissimilar metals. The length, stiffness, cross-sectional shape and/or size or other physical attribute may differ between individual wire members 14. By way of non-limiting example, individual wire members 14 may have circular or non-circular cross-sectional shapes, such as rectangular or triangular cross-sectional shapes. For instance, some or all of the individual wire members 14 may be formed from flat ribbon wires. Furthermore, individual wire members 14 may have irregular, non-uniform cross-sections that vary along the length of the wire member.

In one embodiment, the individual wire members 14 of the metallic braid 12 include a first subset of wire members 16 formed out of or otherwise including platinum, and a second subset of wire members 18 formed out of or otherwise including zirconium. The respective platinum (Pt) wire members 16 and zirconium (Zr) wire members 18 are braided, inter-wound and/or otherwise arranged so that the Pt and Zr material is in physical contact or close proximity at each of a plurality of contact points 20 on the device 10. It will be appreciated that the dissimilar Pt and Zr metallic materials have distinct electrochemical potentials, causing the device 10 to undergo galvanic corrosion at each of the contact points 20 when exposed to an electrolytic medium, such as blood, or other body fluid. More specifically, the Pt material will act as an electrolytic cathode, and the Zr material will act as an electrolytic anode, to thereby create a respective galvanic cell at each contact point 20. These galvanic cells undergo electrochemical corrosion in the presence of electrolytic blood after delivery of the device 10 to a target location within a patient's vasculature, e.g., within an aneurysm. During the galvanic corrosion, a resulting electrochemical potential difference between Pt and Zr develops an electric current that electrolytically oxidizes and expands the zirconium, forming a corrosive product zirconium oxide, $ZrO_2$ ("zirconia") 70 at each contact point 20, thereby stiffening the vaso-occlusive device 10 in-situ. As further described herein, the braided Pt and Zr wires 16 and 18 are preferably constructed and/or otherwise arranged relative to each other so that the galvanic corrosion formation of zirconia at the contact points 20 occurs over time, resulting in a "progressive" in-situ stiffening of the device 10.

It will be appreciated that the particular selection of Zr for the anode material resulting in the formation of zirconia as the corrosive product is highly advantageous, since zirconia comprises a relatively high hardness (about 8.5 Moh's hardness), a relatively high fracture toughness, and is also a highly stable, relatively non-degradable material in blood and other biological fluids. As such, the formation of zirconia at the respective contact points 20 creates a substantially more durable stiffness and over-time strength of the vaso-occlusive device 10, minimizing undesirable migrations and other disadvantages attributed to a relatively low and/or temporal stiffness, and relatively fast degradation, respectively, of the devices disclosed in Rosenbluth et al. and Dehnad.

It will be appreciated that the dissimilar metallic material acting as electrolytic cathode to the zirconium anode may include a number of suitable metallic materials, such as, platinum, iridium, platinum alloys, platinum-tungsten alloy, platinum-iridium alloy, platinum rhenium alloy, platinum palladium alloy, or the like, or suitable combinations thereof. In some embodiments, yttrium may be introduced as an additive to zirconium to form a zirconium-yttrium alloy to be used as one of the dissimilar metallic materials. During galvanic corrosion process, the corrosion product not only contains zirconium dioxide (zirconia), but also yttrium oxide ("yttria"). The presence of yttria in the zirconia corrosion product further stabilizes the zirconia and enhances fracture resistance of the implanted occlusive device. In still other embodiments, elements including (without limitation) calcium, cerium, aluminum, titanium, and hafnium may be added to the zirconium so that calcia, ceria, alumina, or hafnia, respectively, is also formed during the galvanic corrosion process to enhance the stabilization and fracture resistance of the zirconia.

Figure 2A:
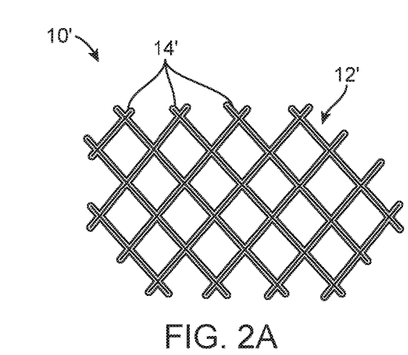
FIGS. 2A-E are perspective and cross-sectional views of a vaso-occlusive device braid constructed according to further embodiments of the disclosed inventions.
Figure 2B:
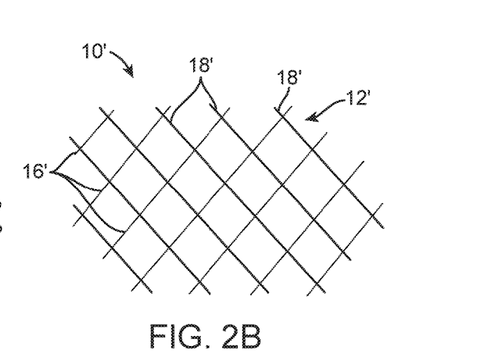
Figure 2C:
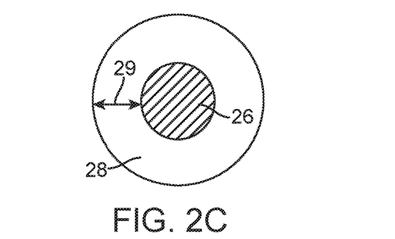
Figure 2D:
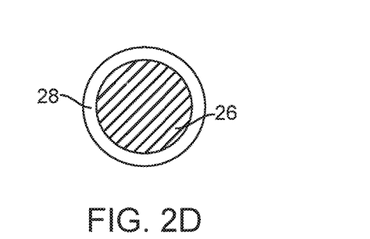
Figure 2E:
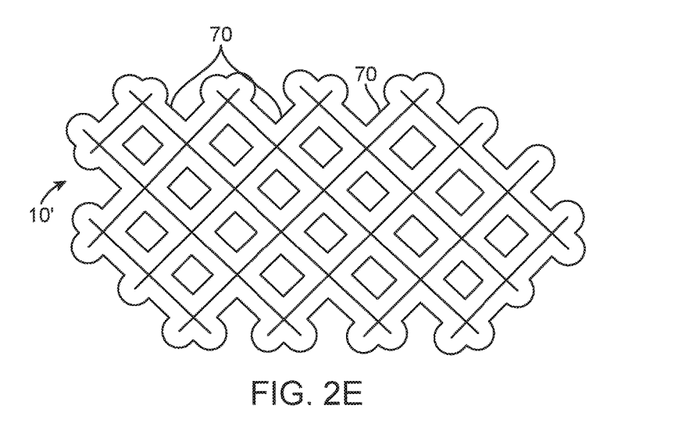

FIGS. 2A-E illustrate alternative embodiments of a vaso-occlusive device 10' constructed in accordance with the disclosed inventions. For ease in illustration and disclosure, the features and configurations of device 10' that are the same as device 10 of FIGS. 1A-B are given the same reference numerals. The vaso-occlusive device 10' comprises a metallic braid 12' formed from a plurality of wire members 14', each wire member 14' having an inner core material 26, preferably one of Pt and Zr, that is at least partially coated, plated, or otherwise covered with an outer coating material 28, preferably the other one of Pt and Zr. The thickness 29 of the coating material 28 can be varied, depending on the desired amount of galvanic corrosion and corrosion products to be produced (FIGS. 2C-D). The coating material can be porous (or "microporous"), wherein the pore size and pore density of the coating material are (again) determined by the desired amount of galvanic corrosion and corrosion products to be produced.

By way of non-limiting example, the core material 26 may be composed of Pt or Pt alloy, which acts as the electrolytic cathode, and the coating material 28 may be composed of Zr or Zr alloy, which acts as the electrolytic anode. Alternatively, the core material 26 may be the electrolytic anode composed of Zr or Zr alloy, and the coating material 28 may be the electrolytic cathode composed of Pt or Pt alloy. In a still further alternative embodiment shown in FIG. 2B, the metallic braid 12' is formed of a first plurality of wires 16', each wire 16' having an electrolytic cathode core 26 composed of Pt or Pt alloy, and an electrolytic anode coating 28 composed of Zr or Zr alloy, and a second plurality of wires 18', each wire 18' having an electrolytic anode core 26 composed of Zr or Zr alloy, and an electrolytic cathode coating 28 composed of Pt or Pt alloy. With each of these embodiments, when the vaso-occlusive device 10' is delivered into an aneurysm and is exposed to blood, the dissimilar metallic Pt and Zr materials undergo a progressive galvanic corrosion, forming zirconia as the corrosive product 70 on the respective wires 16' and 18' (collectively, wires 14'), thereby stiffening the vaso-occlusive device 10' in-situ. The formation of zirconia in the embodiment illustrated in FIG. 2E occurs along and over the plurality of wires 14' themselves, in addition to the contact points 20, since the entire length of each wire of the plurality 14' comprises both Pt and Zr.

Figure 3A:
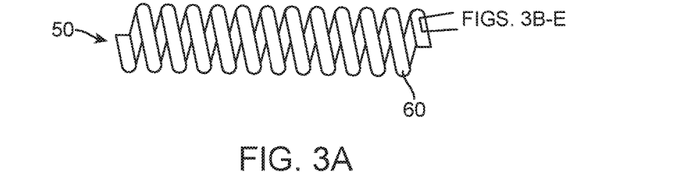
FIGS. 3A-E are cross-sectional views of a vaso-occlusive coil constructed according to various embodiments of the disclosed inventions.
Figure 3B:
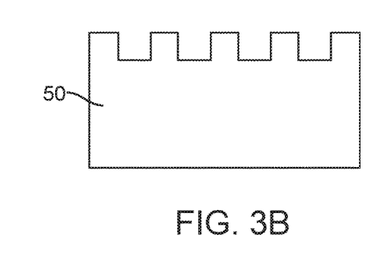
Figure 3C:
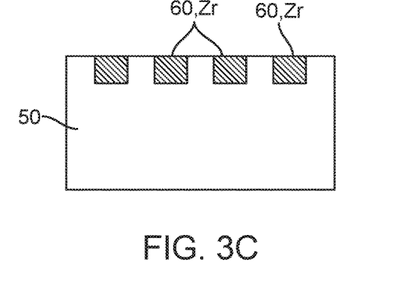
Figure 3D:
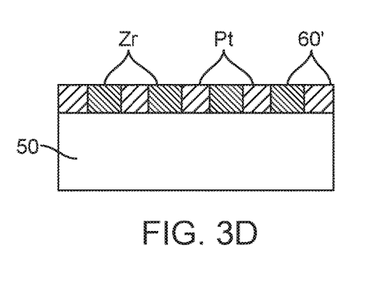
Figure 3E:
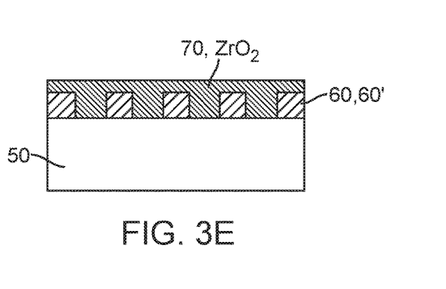

By way of another example, FIGS. 3A-E illustrate a vaso-occlusive coil 50, constructed in accordance with the disclosed inventions. FIGS. 3B-E are cross sectional views of a portion of the coil 50 of FIG. 3A. The coil 50 may be made from a metal, such as pure platinum (Pt). In other embodiments, the coil 50 may be made from an alloy, such as platinum-tungsten alloy (Pt/W), e.g., 8% tungsten and the remainder platinum (Pt). In further embodiments, the coil 50 may be made from platinum-iridium alloy, platinum rhenium alloy, platinum palladium alloy, or any suitable metallic material suitable for forming the electrolytic cathode. The coil 50 further comprises a coating 60 made of zirconium or zirconium alloy acting as electrolytic anode (FIG. 3C). In alternative embodiment, the coil may be made from a neutral material, such as a polymer, with a coating 60' composed of zirconium and platinum (FIG. 3D). The dissimilar metallic materials of the coil 50 (cathode) and coating 60 (anode) (FIG. 3C) or coating 60' (cathode/anode) (FIG. 3D) have distinct electrochemical potentials to undergo a progressive galvanic corrosion (FIG. 3E), when exposed to an electrolytic medium such as blood to thereby expand and create corrosive products 70 that cause in-situ stiffening of the coil 50 in target location, e.g., within an aneurysm.

FIGS. 4A-I illustrate various vaso-occlusive devices 90 constructed in accordance with the disclosed inventions. The vaso-occlusive devices 90 include exemplary arrangements and/or configurations including a plurality of coils 50, such as those shown in FIGS. 3A-E and described above, each coil 50 being formed from dissimilar metallic materials including zirconium or zirconium alloy that are placed into contact or sufficiently close proximity so as to corrode and create expanding oxides and corrosive products including zirconia 70 when exposed to an electrolytic medium, such as blood. Because each contact of two dissimilar metals in the present of blood can form a respective galvanic cell, the coatings 60 may contain numerous individual galvanic cells. Expansion of corrosion material takes up the space between the coils 50, leading to an increase in packing density and in-situ stiffening of the packed coils 50, e.g., after placement of the device 90 within an aneurysm. The degree of the expansion can be optimized based on the application and coating properties, such as material selection, coating thickness, and microstructure. Since the galvanic corrosion occurs over time, the in-situ stiffening of the coils 50 is progressive.

Figure 4A:
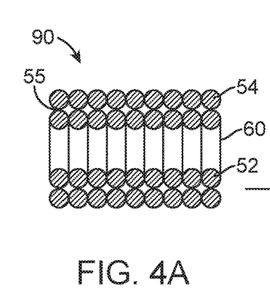
FIGS. 4A-I are sectional views of vaso-occlusive devices constructed according to additional and alternative embodiments of the disclosed inventions.
Figure 4B:
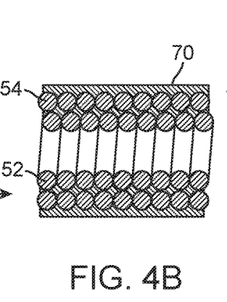

FIGS. 4A-B illustrate a vaso-occlusive device 90 having a layered coil configuration, in which an inner coil 52 is coaxially disposed within an outer coil 54 lumen 55. At least one of coils 52 or 54 is composed of dissimilar metallic materials (e.g., Pt and Zr), including coatings 60, as described above in coil 50. In one embodiment, both coils 52 and 54 comprise at least two dissimilar metallic materials (e.g., Pt and Zr) to undergo the galvanic corrosion when exposed to an electrolytic medium, so that the vaso-occlusive device 90 is progressively stiffened and additionally bonded in-situ (FIG. 4B).

Figure 4C:
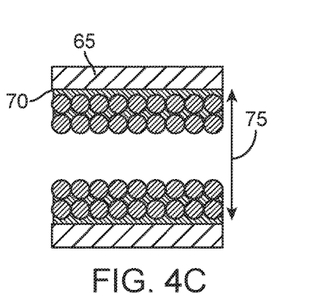

FIG. 4C illustrates an alternative embodiment of the device 90 having an adjacent member 65, e.g., a tubular member, braided layer, stent, coil, or the like, disposed over the outer coil 54 and covering the layered coil configuration. When the galvanic corrosion occurs, the anode material of the vaso-occlusive device 90 expands, creating corrosive products 70 and causing compression 75 to the adjacent member 65, which leads to in-situ stiffening and further bonding of the device 90.

Figure 4D:
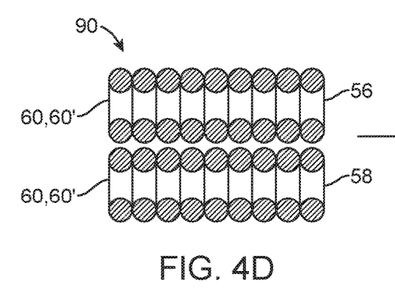
Figure 4E:
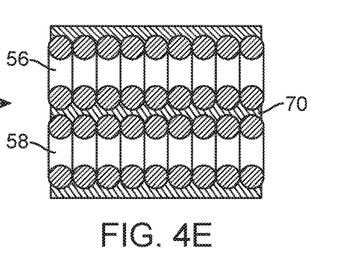

FIGS. 4D-E illustrate another alternative vaso-occlusive device 90 having a layered coil configuration, in which a first coil 56 is adjacently disposed from a second coil 58 (e.g., parallel or lateral). At least one of coils 56 or 58 is composed of dissimilar metallic materials and/or having the coatings 60, as described above with respect to coil 50. In one embodiment, each of the coils 56 and 58 comprise the coating 60' including two dissimilar metallic materials (e.g., platinum and zirconium). When the vaso-occlusive device 90 is exposed to electrolytic blood when placed in the vasculature, it undergoes galvanic corrosion creating the corrosive products 70, creating in in-situ stiffening and bonding of the coils 56 and 58.

Figure 4F:
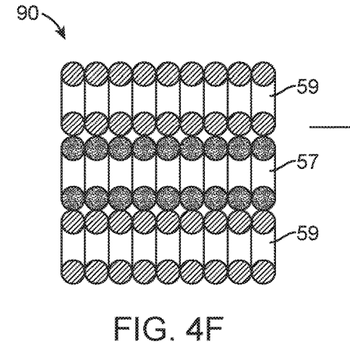
Figure 4G:
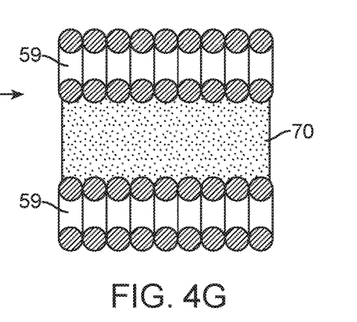

FIGS. 4F-G illustrate still another alternative vaso-occlusive device 90 having a layered coil configuration with a plurality of coils, including a first coil 57 composed of an electrolytic anode material, e.g., Zr, disposed between at least two additional coils 59 composed of an electrolytic cathode material, e.g., Pt. During galvanic corrosion after placement in the vasculature, a resulting electrochemical potential difference develops an electric current that electrolytically oxidizes and expands the Zr anode coil 57 forming zirconia as a corrosion product 70 between the two Pt cathode coils 59, thereby stiffening and bonding the vaso-occlusive device 90 in-situ (FIG. 4G).

Figure 4H:
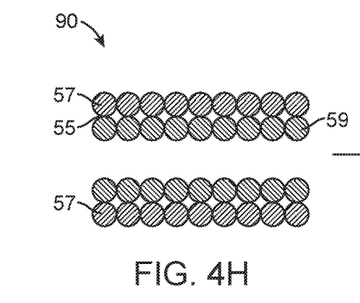
Figure 4I:
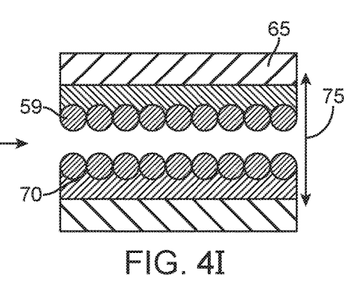

FIGS. 4H-I illustrate yet another alternative vaso-occlusive device 90 having a plurality of coils in a layered coil configuration, in which the cathode coil 59 is coaxially disposed within the lumen 55 of an anode coil 57. The vaso-occlusive device 90 further includes the adjacent member 65 disposed over the outer anode coil 57. Similar to the embodiment illustrated in FIG. 4C, when the galvanic corrosion occurs in FIG. 4I, expansion of the vaso-occlusive device 90 due to the corrosive products 70 causes compression 75 to the adjacent member 65, resulting in progressive in-situ stiffening and bonding of the vaso-occlusive device 90.

FIGS. 5A-F illustrate additional vaso-occlusive devices 100 constructed in accordance with the disclosed inventions. The vaso-occlusive devices 100 may include a braid 101 to further strengthen the in-situ stiffening of the devices 100 and retain the corrosion products 70 formed by the galvanic corrosion of the dissimilar metallic materials including zirconium or zirconium alloy. The corrosion products 70 formed with, on, or around the braid 101 would further support the in-situ stiffening efficiency of the vaso-occlusive devices 100. It will be appreciated that having a braid in the vaso-occlusive devices 100 would increase the amount of galvanic corrosion cells, since the braid creates more surface areas. After galvanic corrosion, the braid would become stiffer as the contact points of the wires forming the braid would be fixed in place by the corrosion products including zirconia 70, thus strengthening the vaso-occlusive devices 100 in-situ. The braid 101 may be composed of suitable biocompatible materials. Alternatively, braids 10 and 10' of FIGS. 1A-2E may be used in the vaso-occlusive devices 100 of FIGS. 5A-F.

Figure 5A:
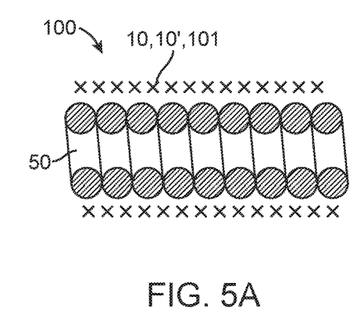
FIGS. 5A-F are sectional views of vaso-occlusive devices constructed according to still further additional and alternative embodiments of the disclosed inventions.
Figure 5B:
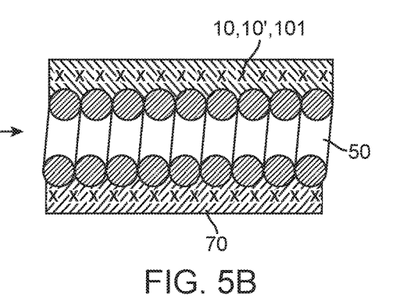

The vaso-occlusive device 100 of FIGS. 5A-B includes at least one vaso-occlusive coil 50, and at least one braid, 10, 10' or 101. When the braid 101 is used in the vaso-occlusive device 100, the coil 50 includes the at least two dissimilar metallic materials, for example in the coating 60, to undergo galvanic corrosion. In other embodiments, one or both of the coil 50 and braid 10, 10' include the at least two dissimilar metallic materials, for example, in coatings 60 and 28, respectively, to undergo galvanic corrosion and thereby cause in-situ stiffing of the vaso-occlusive device 100. As with the above-described embodiments, the metallic material forming the electrolytic anode is zirconium or zirconium alloy.

Figure 5C:
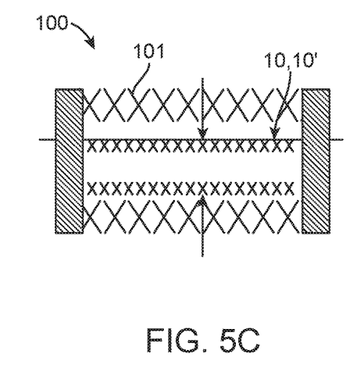
Figure 5D:
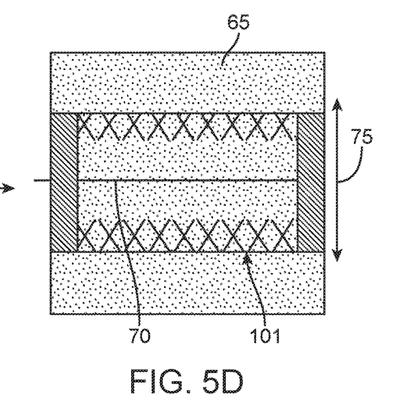
Figure 5E:
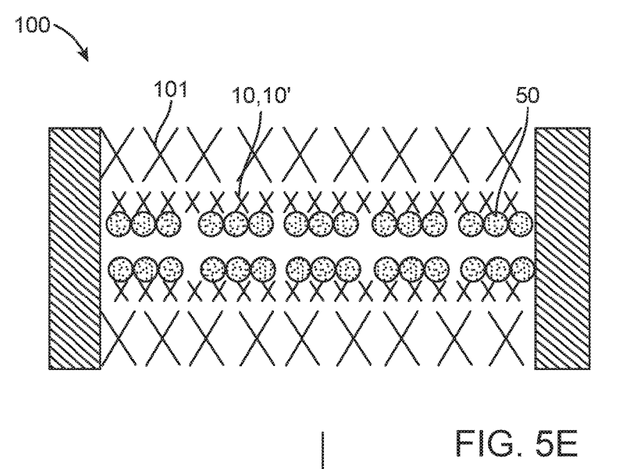
Figure 5F:
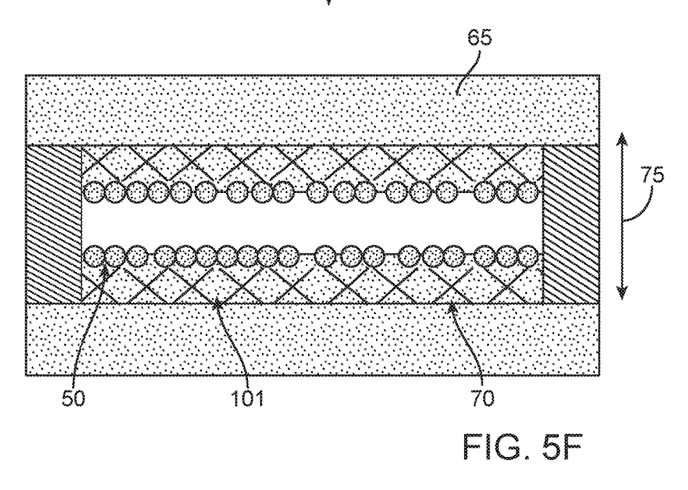

FIGS. 5C-D illustrate another alternative vaso-occlusive device 100 having at least two braids, an inner braid 10, 10' coaxially disposed within an outer braid 101. In alternative embodiments, the outer braid may also include the at least two dissimilar metallic materials, or just the outer braid may include the at least two dissimilar metallic materials (not shown). FIGS. 5E-F illustrate another alternative vaso-occlusive device 100 having the occlusive device of FIG. 5A coaxially disposed with the braid 101. The vaso-occlusive devices 100 of FIGS. 5D and 5F may further include the adjacent member 65 disposed over the outer braid 101. As with the above-described embodiments, the metallic material forming the electrolytic anode in the vaso-occlusive devices 100 of FIGS. 5D and 5F is zirconium or zirconium alloy. Thus, as with the embodiment illustrated in FIG. 4C, when the galvanic corrosion occurs in FIGS. 5D and 5F, expansion of the vaso-occlusive device 100 by the corrosive zirconia product 70 causes compression 75 to the adjacent member 65 leading to the in-situ stiffening and bonding of the vaso-occlusive device 100.

Although particular embodiments have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. An implantable vaso-occlusive device constructed from a plurality of metallic wires, the one or more wires each comprising:

an inner core; and an outer coating, one of the inner core and the outer coating comprising a first metallic material, and the other of the core and the coating comprising zirconium or zirconium alloy that is electrochemically dissimilar to the first metallic material, the outer coating of each wire haiving a plurality of discrete pores that expose the inner core of the respective wire, such that the device will undergo galvanic corrosion when exposed to blood to create a corrosive product comprising zirconia after the device has been implanted in a vasculature, the one or more wires including a first wire having a core made from platinum or platinum alloy and a coating made from zirconium or zirconium alloy, a second wire having a core made from zirconium or zirconium alloy, and a coating made from platinum or platinum alloy.

2. The vaso-occlusive device of claim 1, wherein the plurality of metallic wires are arranged in a braided configuration.

3. The vaso-occlusive device of claim 2, wherein the braided configuration comprises a tubular sleeve configuration.

4. The vaso-occlusive device of claim 2, wherein at least one wire of the plurality varies with at least one other wire of the plurality in one or more of a length, a stiffness, a cross-sectional shape, and a size.

5. The vaso-occlusive device of claim 2, wherein at least one wire of the plurality has a non-circular cross-sectional shape.

6. The vaso-occlusive device of claim 1, wherein the one or more metallic wires are wound into a helical coil configuration.

7. The vaso-occlusive device of claim 1, wherein the platinum alloy comprises one of platinum tungsten alloy, platinum-iridium alloy, platinum-rhenium alloy, and platinum-palladium alloy, and wherein the zirconium alloy comprises one of zirconium-cerium alloy, zirconium-yttrium alloy, zirconium-titanium alloy, zirconium-aluminum alloy, zirconium-calcium alloy, and zirconium-hafnium alloy.

* * * * *